(12) United States Patent
Kai et al.

(10) Patent No.: US 6,204,410 B1
(45) Date of Patent: Mar. 20, 2001

(54) ETHER COMPOUNDS AND PROCESS FOR PRODUCING THE SAME

(75) Inventors: Kazufumi Kai; Keisuke Ohta; Hiroshi Uchida, all of Oita (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/254,595

(22) PCT Filed: Jul. 10, 1998

(86) PCT No.: PCT/JP98/03107

§ 371 Date: Mar. 11, 1999

§ 102(e) Date: Mar. 11, 1999

(87) PCT Pub. No.: WO99/02482

PCT Pub. Date: Jan. 21, 1999

(30) Foreign Application Priority Data

Jul. 11, 1997 (JP) .................................................. 9-186804

(51) Int. Cl.<sup>7</sup> .................................................. C07C 67/48
(52) U.S. Cl. ............................................. 560/190; 560/198
(58) Field of Search ...................................... 560/190, 198

(56) References Cited

U.S. PATENT DOCUMENTS 4,864,054  9/1989  Crivello et al. .

FOREIGN PATENT DOCUMENTS 575987  5/1959  (CA) .
B-55-39533  10/1980  (JP) .
2744849  2/1998  (JP) .

OTHER PUBLICATIONS

Crivello, J.V. and Kim, Whan–Gi, "Synthesis and photopolymerization of multifunctional propenyl ether monomers", *J.M.S.—Pure Appl. Chem.*, A31(9), pp. 1105–1119 (1994).

*Primary Examiner*—Paul J. Killos
(74) *Attorney, Agent, or Firm*—Sughrue, Mion, Zinn, Macpeak & Seas, PLLC

(57) ABSTRACT

Disclosed herein is a novel propenyl ether compound which can be cured by radical polymerization.

The invention provides a propenyl ether compound represented by the formula:

$$CH_3-CH=CH-(OR^1)_n-OCO-X-COO-(R^2O)_n-CH=CH-CH_3 \qquad (1)$$

wherein X represents —CH=CH— or —CH$_2$—C(=CH$_2$)—, each of R$^1$ and R$^2$ represents an alkylene group having 2 to 4 carbon atoms or a cycloalkylene group having 5 to 12 carbon atoms, and n is an integer of 1 to 5, and an allyl ether compound represented by the formula:

$$CH_2=CH-CH_2-(OR^6)_n-OCO-X-COO-(R^7O)_n-CH_2-CH=CH_2 \qquad (2)$$

wherein X represents —CH=CH— or —CH$_2$—C(=CH$_2$)—, each of R$^6$ and R$^7$ independently represents an alkylene group having 2 to 4 carbon atoms or a cycloalkylene group having 5 to 12 carbon atoms, and n is an integer of 1 to 5, provided that, when n=1, each of R$^6$ and R$^7$ represents an alkylene group having 3 or 4 carbon atoms or a cycloalkylene group having 5 to 12 carbon atoms.

The above compounds can be obtained by the reaction between fumaric acid, maleic acid, itaconic acid, a derivative thereof or the like and a polyalkylene glycol monopropenyl ether, a polyalkylene glycol monoallyl ether or the like. Further, the compound of the formula (1) can be obtained by isomerizing the allyl ether compound.

10 Claims, No Drawings

ETHER COMPOUNDS AND PROCESS FOR PRODUCING THE SAME

TECHNICAL FIELD

The present invention relates to a novel compound having an ether group, which can be cured by radical polymerization and a process for producing the same.

BACKGROUND ART

Thermosetting resins and photocurable resins are used as coating materials, paint materials, optical materials and adhesive materials. Curable compositions exhibiting a high curing rate that contain an acrylic acid ester or methacrylic acid ester as a principal component are widely used as thermosetting resins from the viewpoint that the operation efficiency and productivity can be enhanced. In particular, a bifunctional or higher-functional acrylic acid ester or methacrylic acid ester is employed for increasing the polymerization degree of cured resin to thereby increase the hardness of the surface of the cured resin.

However, in the curing of such a polyfunctional acrylic acid ester by radical polymerization, the polymerization is inhibited by oxygen to thereby produce uncured portion with the result that the problem of remaining tack is caused. Moreover, many of the acrylic acid esters exhibit high skin stimulation, so that, also, the problem of toxicity is encountered.

Vinyl ether compounds are known as being a photocurable compound whose skin stimulation is low. The vinyl ether compounds are cured by cationic polymerization, so that they are less susceptible to the polymerization inhibition by oxygen. However, the catalysts for use in the cationic polymerization have such drawbacks that they are deactivated by moisture or bases, they are expensive and the number of varieties thereof is small to thereby limit the number of really available catalysts and many thereof are highly toxic. Further, the radical polymerization of only one kind (single) vinyl ether does not proceed, so that, for example, the method of copolymerizing a vinyl ether and an acrylic material (monomer) is employed for effecting the radical polymerization. However, in this copolymerization, the copolymerizability cannot always be stated as being excellent and, even if the copolymerization by radical polymerization is performed, the production of product with satisfactorily high practicability is limited.

Recently, the use of a propenyl ether as a cationic polymerization material is drawing attention. Crivello et al. reported in J. Macromol. Sci. Part A, A31(9), 1105 (1994) that propenyl ethers exhibited high cationic polymerizability. The propenyl ether compounds have skeletal structures derived from phenols such as bisphenol.

Further, U.S. Pat. No. 4,864,054 reported that an aromatic propenyl ether compound could be used in various applications through the cationic polymerization thereof. This aromatic propenyl ether compound is one having a skeletal structure derived from a phenol such as bisphenol A or hydroquinone or from an ester such as a terephthalic acid ester or an isophthalic acid ester.

However, when the radical polymerization is intended, the problem is encountered such that the radical polymerizability of this propenyl ether alone is as low as that of the above vinyl ether.

The radical polymerization method has advantages in that, as compared with other polymerization methods, the curing time is generally relatively short, the molecular weight can be large, a large variety of radical polymerization initiators are available and their use is easy. Therefore, the radical polymerization method is an industrially useful polymerization method. However, a compound having a propenyl ether group or an allyl ether group whose sole radical polymerization is practicable is little known.

(1) Canadian Patent Specification No. 575985 describes esters prepared from a saturated or an unsaturated polycarboxylic acid and a β-(2-propenoxy)alkanol of the formula RCH=CH—CH$_2$—O—CH(R')CH(R")—OH or CH$_2$=C(R)—CH$_2$—O—CH(R')CH(R")—OH (wherein each of R, R' and R" is selected from among hydrogen and alkyls, the alkyls preferably being those which do not contain more than three carbon atoms, for example, methyl, ethyl or propyl).

Specifically, the specification discloses, as preferred esters, di-(β-propenoxyethyl) maleate, di(β-propenoxyethyl) fumarate (CH$_2$=CH—CH$_2$—O—(CH$_2$)$_2$—OCO—CH=CH—COO—(CH$_2$)$_2$—O—CH$_2$—CH=CH$_2$) and di-(β-propenoxyethyl) itaconate (CH$_2$=CH—CH$_2$—O—(CH$_2$)$_2$—OCO—CH(=CH$_2$)CH$_2$—COO—(CH$_2$)$_2$—O—CH$_2$—CH=CH$_2$). Further, the specification teaches that the copolymerization reaction of the above monomers is accelerated by the presence of a peroxide such as dibenzoyl peroxide or diacetyl peroxide.

However, the specification fails to present any specific description as to esters including an alkylene group having at least 3 carbon atoms or a cycloalkylene group having at least 5 carbon atoms in the moiety "CH(R')—CH(R")—" of the above formula.

(2) Japanese Patent Publication No. 55(1980)39533 discloses a process for producing an ω-vinyloxyalkyl carboxylate in which an unsaturated carboxylic acid and an ω-halogenoalkyl vinyl ether are condensed with each other.

(3) Further, Japanese Patent Laid-open Publication No. 57(1982)-165409 discloses a thermosetting composition containing a thermosetting catalyst, which comprises:

(A) an aromatic polyvinyl ether compound selected from among (i) polyvinyl compounds of the formula R[QR$^1$OC(R$^2$)=C(R$^3$)$_2$]$_n$ (wherein Q: —O—, —COO—, etc., R: polyvalent aromatic organic group, R$^1$: alkylene group having 1 to 8 carbon atoms, each of R$^2$ and R$^3$: H or alkyl group having 1 to 8 carbon atoms, and n: 2 to 10) and (ii) reaction product of the above polyvinyl compound with an active hydrogen compound selected from a specified group including polycarboxylic acids, phenols, etc., and (B) (a) an aryl onium salt selected from a specified group and (b) an organic oxidant or an aromatic polyvinyl ether soluble copper compound.

(4) Still further, Japanese Patent No. 2,744,849 describes a process for producing a polyester having vinyl ether terminals, which comprises the steps of:

(a) reacting a polyol with a polybasic acid ester having vinyl ether terminals in the presence of a transesterification catalyst to thereby produce an oligomer of the polyol and the polybasic acid ester which has vinyl ether terminals and a by-product of hydroxymonovinyl ether, and (b) separating the hydroxymonovinyl ether during the reaction of the step (a).

Compounds of the formula Y-[COOX]$_m$ (wherein Y: alkyl group, etc., X: alkyl having 1 to 6 carbon atoms, etc., and m is 2 to 6) in which Y may be —(CH$_2$)$_n$— are described as the above polybasic acid ester. The reaction of the formula:

XOCO—Y—COOX (i)+R'CH=CR"OZ-OH (ii)→

R'CH=CR"OZ—OCO—Y—COO—ZOR"C=HCR'(iii)+2XOH↑

(wherein each of R' and R": H or lower alkyl group having 1 to 10 carbon atoms and Z: alkylene group or cycloalkylene group) and the chain extension reaction between vinyl ether terminated ester (iii) and polyol (HO-A-OH) are described as examples of the vinyl ether terminal forming reactions of ester.

However, in the patent specification, there is no description regarding compounds wherein Y represents —CH=CH or —(CH$_2$)—C(=CH$_2$)—, and there is no description teaching or suggesting the radical polymerization of vinyl ether terminated ester (iii).

(5) Still further, claim 1 of Published Japanese Translation of PCT Patent Application No. 5(1993)-506838 describes an optical fiber coating composition comprising a product obtained by reacting together (a) a vinyl ether urethane oligomer composed of a product obtained by reacting together (i) a hydroxyl terminated polyester or hydroxyl terminated polyether, (ii) a diisocyanate or a polyisocyanate having at least two functional groups and (iii) a hydroxy-monovinyl ether, (b) a vinyl ether terminated ester monomer and (c) a vinyl ether terminated monomer derived from a specified alcohol. A-(—COOZOCR$_4$=CHR$_3$)$_n$ (wherein n: 1 to 4, A: alkylene group, etc., Z: alkylene, etc., each of R$_3$ and R$_4$: H or alkyl group having 1 to 10 carbon atoms) is described as representing the above vinyl ether terminated ester monomer (b). In claim 3 thereof, —CH=CH—, etc. are listed as the above A, and —(CH$_2$)$_4$—O—(CH$_2$)$_4$—, —(CH$_2$)4—O—(CH$_2$)$_4$—O—(CH$_2$)$_4$—, —CH$_2$CH$_2$—O—CH$_2$CH$_2$—, etc. are listed as the above Z. The specification also describes a composition comprising the above composition and a cationic polymerization initiator, etc.

However, although the specification describes an embodiment in which a cationic polymerization is performed with the use of a cationic photoinitiator of a triarylphosphonium hexafluorophosphate salt (Ar$_3$SPF$_6$) (Union Carbide UVI-6960), there is no example performing the radical polymerization of the vinyl ether terminated ester monomer (b). As apparent therefrom, the specification neither describes any technical concept of effecting the radical polymerization of the above vinyl ether terminated ester monomer (b) nor suggests any technical concept of adding a radical polymerization initiator to the above composition containing the monomer (b) to thereby carry out the radical polymerization.

OBJECT OF THE INVENTION

The present invention has been made with a view toward resolving the above problems of the prior art, and it is an object of the present invention to provide a propenyl ether compound and an allyl ether compound capable of radical polymerization.

It is another object of the present invention to provide a process for producing the above propenyl ether compound and allyl ether compound for use in radical polymerization.

DISCLOSURE OF THE INVENTION

The propenyl ether compound for use in radical polymerization according to the present invention is represented by the formula:

CH$_3$—CH=CH—(OR$^1$)$_n$—OCO—X—COO—(R$^2$O)$_n$—CH=CH—CH$_3$ (1)

wherein X represents —CH=CH— or —CH$_2$—C(=CH$_2$)—, each of R$^1$ and R$^2$ represents an alkylene group having 2 to 4 carbon atoms or a cycloalkylene group having 5 to 12 carbon atoms, and n is an integer of 1 to 5.

In the present invention, it is preferred that, in the formula (1), n=1 and each of R$^1$ and R$^2$ represents —CH$_2$—CH$_2$— or —CH$_2$—CH(—CH$_3$)—.

Further, in the present invention, it is preferred that, in the formula (1), n=1, each of R$^1$ and R$^2$ represents —CH$_2$—CH$_2$— or —CH$_2$—CH(—CH$_3$)—, and X represents —CH=CH— (trans).

The first process for producing the propenyl ether compound for use in radical polymerization according to the present invention comprises subjecting:

an ester represented by the formula R$^3$—OCO—X—COO—R$^4$ (wherein X represents —CH=CH— or —CH$_2$—C(=CH$_2$)— and each of R$^3$ and R$^4$ independently represents an alkenyl group or alkyl group having 1 to 3 carbon atoms) and an alcohol represented by the formula CH$_3$—CH=CH—(OR$^5$)$_n$—OH (wherein R$^5$ represents an alkylene group having 2 to 4 carbon atoms or a cycloalkylene group having 5 to 12 carbon atoms, and n is an integer of 1 to 5)

to a transesterification reaction conducted in the presence of a transesterification catalyst to thereby obtain the above propenyl ether compound.

The second process for producing the propenyl ether compound for use in radical polymerization according to the present invention comprises isomerizing an allyl ether compound represented by the formula:

CH$_2$=CH—CH$_2$—(OR$^6$)$_n$—OCO—X—COO—(R$^7$O)$_n$—CH$_2$—CH=CH$_2$ (2)

wherein X represents —CH=CH— or —CH$_2$—C(=CH$_2$)—, each of R$^6$ and R$^7$ independently represents an alkylene group having 2 to 4 carbon atoms or a cycloalkylene group having 5 to 12 carbon atoms, and n is an integer of 1 to 5, to thereby obtain the above propenyl ether compound.

The third process for producing the propenyl ether compound for use in radical polymerization according to the present invention comprises subjecting:

(i) at least one carboxylic acid or anhydride thereof selected from the group consisting of maleic anhydride, maleic acid, fumaric acid, itaconic acid and itaconic anhydride, and (ii) an alcohol represented by the formula CH$_2$=CH—CH$_2$—(OR$^8$)$_n$—OH (wherein R$^8$ represents an alkylene group having 2 to 4 carbon atoms or a cycloalkylene group having 5 to 12 carbon atoms, and n is an integer of 1 to 5)

to an esterification reaction conducted in the presence of an esterification catalyst to thereby obtain the allyl ether compound of the above formula (2), and isomerizing the allyl ether compound to thereby obtain the above propenyl ether compound.

The fourth process for producing the propenyl ether compound for use in radical polymerization according to the present invention comprises subjecting:

an ester represented by the formula R$^3$—OCO—X—COO—R$^4$ (wherein X represents —CH=CH—or —CH$_2$—C(=CH$_2$)— and each of R$^3$ and R$^4$ represents an alkenyl group or alkyl group having 1 to 3 carbon atoms) and an alcohol represented by the formula CH$_2$=CH—CH$_2$—(OR$^8$)$_n$—OH (wherein R$^8$ represents an alkylene group having 2 to 4 carbon atoms or a cycloalkylene group having 5 to 12 carbon atoms, and n is an integer of 1 to 5)

to a transesterification reaction conducted in the presence of a transesterification catalyst to thereby obtain the allyl ether compound of the above formula (2), and isomerizing the allyl ether compound to thereby obtain the above propenyl ether compound.

In the present invention, it is preferred that the isomerization be performed in the presence of an isomerization catalyst comprising a metal salt, a metal complex, or a catalyst supporting a metal, which metal is at least one metal selected from among the metals of Group 8 of the periodic table.

Further, in the present invention, it is preferred that said isomerization catalyst comprises a metal salt, a metal complex, or a catalyst supporting a metal, which metal is at least one metal selected from among ruthenium, palladium, rhodium, platinum and iridium.

Still further, in the present invention, it is preferred that, in the isomerization of the allyl ether compound of the formula (2), an allyl ether group be isomerized into a propenyl ether group corresponding thereto at a conversion of at least 50%.

The allyl ether compound for use in radical polymerization according to the present invention is represented by the above formula (2), wherein, provided that it is preferred that, when n=1, each of $R^6$ and $R^7$ independently represents an alkylene group having 3 or 4 carbon atoms or a cycloalkylene group having 5 to 12 carbon atoms.

The first process for producing the allyl ether compound for use in radical polymerization according to the present invention comprises subjecting:

(i) at least one unsaturated dicarboxylic acid or anhydride thereof selected from the group consisting of maleic anhydride, maleic acid, fumaric acid, itaconic acid and itaconic anhydride, and (ii) an alcohol represented by the formula $CH_2$=CH—$CH_2$—$(OR^8)_n$—OH (wherein $R^8$ represents an alkylene group having 2 to 4 carbon atoms or a cycloalkylene group having 5 to 12 carbon atoms, and n is an integer of 1 to 5, provided that, when n=1, it is preferred that $R^8$ represent an alkylene group having 3 or 4 carbon atoms or a cycloalkylene group having 5 to 12 carbon atoms) to an esterification reaction conducted in the presence of an esterification catalyst, to thereby obtain the above allyl ether compound for use in radical polymerization.

The second process for producing the allyl ether compound for use in radical polymerization according to the present invention comprises subjecting:

an ester represented by the formula $R^3$—OCO—X—COO—$R^4$ (wherein X represents —CH=CH— or —$CH_2$—C(=$CH_2$)— and each of $R^3$ and $R^4$ independently represents an alkenyl group or alkyl group having 1 to 3 carbon atoms) and an alcohol represented by the formula $CH_2$=CH—$CH_2$—$(OR^8)_n$—OH (wherein $R^8$ represents an alkylene group having 2 to 4 carbon atoms or a cycloalkylene group having 5 to 12 carbon atoms, and n is an integer of 1 to 5, provided that, when n=1, it is preferred that $R^8$ represents an alkylene group having 3 or 4 carbon atoms or a cycloalkylene group having 5 to 12 carbon atoms)

to a transesterification reaction conducted in the presence of a transesterification catalyst to thereby obtain the above allyl ether compound for use in radical polymerization.

The process for producing an ether (co)polymer according to the present invention comprises performing a radical polymerization of any of the above propenyl ether compounds for use in radical polymerization or the allyl ether compound for use in radical polymerization in the presence of a radical polymerization initiator to thereby obtain the above (co)polymer.

The present invention provides the propenyl ether compound and allyl ether compound for use in radical polymerization.

The present invention provides the process for producing the above propenyl ether compound and allyl ether compound for use in radical polymerization.

BEST MODE FOR CARRYING OUT THE INVENTION

The propenyl ether compound for use in radical polymerization, allyl ether compound for use in radical polymerization, process for producing these compounds and method of performing radical polymerization of these compounds according to the present invention will be described in detail below. In the following description, when the same character is employed in different chemical formulae, it represents the same group or compound unless otherwise specified.

Propenyl Ether Compound for Use in Radical Polymerization

The propenyl ether compound for use in radical polymerization according to the present invention is represented by the formula:

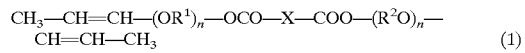

$CH_3$—CH=CH—$(OR^1)_n$—OCO—X—COO—$(R^2O)_n$—CH=CH—$CH_3$     (1)

wherein X represents —CH=CH— or —$CH_2$—C(=$CH_2$)—, each of $R^1$ and $R^2$ represents an alkylene group having 2 to 4 carbon atoms or a cycloalkylene group having 5 to 12 carbon atoms, and n is an integer of 1 to 5.

This propenyl ether compound for use in radical polymerization (1) has propenyl ether groups (—O—CH=CH—$CH_3$) at both terminals thereof and, in its molecule, has an unsaturated dibasic acid residue (unsaturated dicarboxylic acid radical) represented by the formula —O—X—CO—, such as maleic acid residue (i), fumaric acid residue (ii) or itaconic acid residue (iii), namely,

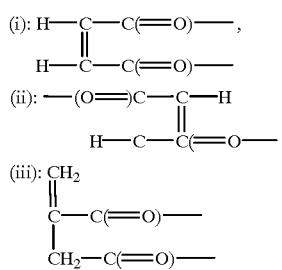

The propenyl ether group (—O—CH=CH—$CH_3$) has E-form and Z-form. In the formula (1), the propenyl ether group may be of either E-form or Z-form, and the ratio thereof is not particularly limited.

When X is —CH=CH—, there are two types, namely cis and trans, and the cis type corresponds to the above formula (i) while the trans type corresponds to the above formula (ii). On the other hand, when X is —CH$_2$—C(=CH$_2$)—, the compound corresponds to the above formula (iii).

Generally, the compound containing a propenyl ether group exhibits high cationic polymerizability but low radical polymerizability. However, in the present invention, the propenyl ether group is combined with the unsaturated dibasic acid residue such as maleic acid residue, fumaric acid residue or itaconic acid residue, so that the propenyl ether group and the double bond of the unsaturated dibasic acid residue exert copolymerizability to thereby enable the radical polymerization. Moreover, in the present invention, there are both propenyl ether group and unsaturated dibasic acid residue having a double bond in the same molecule, so that a high degree of crosslinking is attained at the time of curing to thereby reduce the proportion of uncured portion with the result that an excellent cured product can be obtained.

In the present invention, the propenyl ether compound of the formula (1) in which R$^1$ and R$^2$ are —CH$_2$—CH$_2$— (including both trans and cis, this applies hereinafter) or —CH$_2$CH(CH$_3$)— and n is 1 is preferred because an excellent cured product is obtained.

In the present invention, the compound of the formula (1) in which X represents the unsaturated double bond derived from fumaric acid —CH=CH— (trans) is especially preferred. The propenyl ether group and the double bond derived from fumaric acid are especially excellent in radical copolymerizability.

Production of the Propenyl Ether Compound for Use in Radical Polymerization (1)

The above propenyl ether compound for use in radical polymerization (1) is produced by the following various processes.

Specifically, the propenyl ether compound (1) can be synthesized by a transesterification of an ester represented by the following formula (4-a) and an alcohol represented by the following formula (4-b):

R$^3$—OCO—X—COO—R$^4$ (4-a)

wherein X represents —CH=CH— or —CH$_2$—C (=CH$_2$)— and each of R$^3$ and R$^4$ independently represents an alkenyl group or alkyl group having 1 to 3 carbon atoms, and

CH$_3$—CH=CH—(OR$^5$)$_n$—OH (4-b)

wherein R$^5$, like R$^1$ or R$^2$ of the formula (1), represents an alkylene group having 2 to 4 carbon atoms or a cycloalkylene group having 5 to 12 carbon atoms, and n, like n of the formula (1), is an integer of 1 to 5.

The above ester (4-a) is a lower alkyl ester or lower alkenyl ester of an unsaturated dibasic acid (unsaturated dicarboxylic acid) such as maleic acid, fumaric acid or itaconic acid.

This ester (4-a), namely the lower alkyl ester or lower alkenyl ester of an unsaturated dibasic acid, is, for example, one which contains an alkyl or alkenyl group having 1 to 3 carbon atoms. Specifically, for example, the ester (4-a) includes lower alkyl esters of maleic acid, such as dimethyl maleate, diethyl maleate, dipropyl maleate and diisopropyl maleate;

lower alkenyl esters of maleic acid, such as diallyl maleate;

lower alkyl esters of fumaric acid, such as dimethyl fumarate, diethyl fumarate, dipropyl fumarate and diisopropyl fumarate;

lower alkenyl esters of fumaric acid, such as diallyl fumarate;

lower alkyl esters of itaconic acid, such as dimethyl itaconate, diethyl itaconate, dipropyl itaconate and diisopropyl itaconate; and lower alkenyl esters of itaconic acid, such as diallyl itaconate.

With respect to the alkyl or alkenyl ester which contains an alkyl or alkenyl group having 4 or more carbon atoms, the removal of by-products from the reaction system tends to be difficult because the boiling point of alkyl alcohol or alkenyl alcohol secondarily produced with the advance of the reaction is high.

The above alcohol (4-b) includes, for example, polyalkylene glycol monopropenyl ethers in which R$^5$ is an alkylene group and polycycloalkylene glycol monopropenyl ethers in which R$^5$ is a cycloalkylene group.

Specifically, for example, the above alcohol (4-b) includes:

polyalkylene glycol monopropenyl ethers in which R$^5$ is an alkylene group, such as ethylene glycol monopropenyl ether, propylene glycol monopropenyl ether, 1,3-propanediol monopropenyl ether, 1,4-butanediol monopropenyl ether, 1,3-butanediol monopropenyl ether, 1,2-octanediol monopropenyl ether, diethylene glycol monopropenyl ether, dipropylene glycol monopropenyl ether, triethylene glycol monopropenyl ether, tripropylene glycol monopropenyl ether, tetraethylene glycol monopropenyl ether and tetrapropylene glycol monopropenyl ether; and polycycloalkylene glycol monopropenyl ethers in which R$^5$ is a cycloalkylene group, such as 1,2-cyclopentanediol monopropenyl ether, 1,2-cyclohexanediol monopropenyl ether and 1,2-cyclododecanediol monopropenyl ether.

These polyalkylene or polycycloalkylene glycol monopropenyl ethers (4-b) are preferably used in an amount of 1 to 10-fold mol, still preferably 1.1 to 3-fold mol, relative to the ester group equivalent of the above ester (4-a), namely the ester group equivalent of the lower alkyl ester or lower alkenyl ester of maleic acid, fumaric acid or itaconic acid.

Conventional transesterification catalysts can be used in this transesterification reaction. Examples of preferably used catalysts include:

alkali metals, alkaline earth metals, oxides thereof and weak acid salts of these metals;

oxides, hydroxides, alcoholates, organic acid salts (e.g., zinc acetate) and acetylacetonato complexes of Mn, Zn, Zr, Cd, Ti, Pb, Co and Sn; and dibutyltin oxide and dioctyltin oxide.

These catalysts are generally used in an amount of 0.01 to 5% by weight, preferably 0.05 to 1% by weight, based on the total amount of the above ester (4-a) such as a lower alkyl or alkenyl ester of maleic acid, fumaric acid or itaconic acid.

The reaction can generally be performed at 80 to 200° C., preferably 120 to 180° C., under atmospheric or superatmospheric pressure. When the reaction temperature exceeds 200° C., a thermal polymerization is likely to occur.

It is preferred that this transesterification reaction be performed in an atmosphere of inert gas such as nitrogen gas.

During the reaction, the polymerization may be prevented by the addition of, for example, the below described phenolic polymerization inhibitor.

The reaction is advanced by distilling secondarily produced alkyl alcohol or alkenyl alcohol off the reaction system. The reaction can be finalized by the removal of secondarily produced alkyl alcohol or alkenyl alcohol under reduced pressure.

The propenyl ether compound (1) obtained by the above transesterification of ester (4-a) and alcohol (4-b), although can be used as a curable resin while the catalyst remains therein, is occasionally purified before use by, for example, distillation in the presence of the below described polymerization inhibitor.

The propenyl ether compound (1) according to the present invention can be obtained by isomerizing an allyl ether compound (2) represented by the formula:

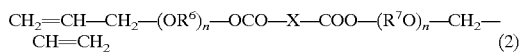

$$CH_2=CH-CH_2-(OR^6)_n-OCO-X-COO-(R^7O)_n-CH_2-CH=CH_2 \quad (2)$$

wherein X represents —CH=CH— or —CH$_2$—C(=CH$_2$)—, each of R$^6$ and R$^7$, like R$^1$ and R$^2$ of the formula (1), independently represents an alkylene group having 2 to 4 carbon atoms or a cycloalkylene group having 5 to 12 carbon atoms, and n is an integer of 1 to 5, to thereby convert the allyl ether group "CH$_2$=CH—CH$_2$—O—" to the propenyl ether group "CH$_3$—CH=CH—O—".

Allyl Ether Compound (2)

Of these allyl ether compounds (2) represented by the above formula (2), it is preferred that, when n=1, each of R$^6$ and R$^7$ independently represent an alkylene group having 3 or 4 carbon atoms or a cycloalkylene group having 5 to 12 carbon atoms.

The allyl ether compound (2) for use can be obtained by subjecting an unsaturated dicarboxylic acid or anhydride thereof, such as maleic anhydride, maleic acid, fumaric acid, itaconic acid or itaconic anhydride, and an alcohol represented by the following formula (5) to an esterification reaction conducted in the presence of an esterification catalyst.

$$CH_2=CH-CH_2-(OR^8)_n-OH \quad (5)$$

wherein R$^8$, like R$^6$ and R$^7$ of the formula (2), represents an alkylene group having 2 to 4 carbon atoms or a cycloalkylene group having 5 to 12 carbon atoms, and n, like n of the formula (2), is an integer of 1 to 5, provided that, when n=1, it is preferred that R$^8$ represents an alkylene group having 3 or 4 carbon atoms or a cycloalkylene group having 5 to 12 carbon atoms.

The alcohol represented by the above formula (5) has the allyl ether group "CH$_2$=CH—CH$_2$—O—" and examples thereof include polyalkylene glycol monoallyl ethers in which R$^8$ of the formula (5) is an alkylene group and polycycloalkylene glycol monoallyl ethers in which R$^8$ is a cycloalkylene group.

Specifically, for example, the above alcohol (5) includes:

polyalkylene glycol monoallyl ethers in which R$^8$ is an alkylene group, such as ethylene glycol monoallyl ether, propylene glycol monoallyl ether, 1,3-propanediol monoallyl ether, 1,4-butanediol monoallyl ether, 1,3-butanediol monoallyl ether, 1,2-octanediol monoallyl ether, diethylene glycol monoallyl ether, triethylene glycol monoallyl ether, tripropylene glycol monoallyl ether, tetraethylene glycol monoallyl ether and tetrapropylene glycol monoallyl ether; and polycycloalkylene glycol monoallyl ethers in which R$^8$, is a cycloalkylene group, such as 1,2-cyclopentanediol monoallyl ether, 1,2-cyclohexanediol monoallyl ether and 1,2-cyclododecanediol monoallyl ether.

The above alcohol (5) is used in an amount of 2 to 10-fold mol, preferably 2.1 to 4-fold mol, relative to the unsaturated dicarboxylic acid or anhydride thereof, such as maleic acid, maleic anhydride, fumaric acid, itaconic acid or itaconic anhydride (total amount thereof).

Conventional esterification catalysts can be used in this esterification reaction. Examples thereof include acid catalysts such as p-toluenesulfonic acid, sulfuric acid and acidic ion exchange resins.

With respect to the amount of these catalysts, p-toluenesulfonic acid, sulfuric acid or the like is generally used in an amount of 0.1 to 5% by weight based on the unsaturated dicarboxylic acid or anhydride thereof, such as maleic anhydride, maleic acid, fumaric acid, itaconic acid or itaconic anhydride (total amount thereof). The amount of acidic ion exchange resin used is generally not limited.

This esterification reaction is generally performed at 60 to 150° C. under atmospheric or superatmospheric pressure while removing water secondarily produced in accordance with the advance of the reaction.

The esterification reaction may be carried out in a solvent according to necessity. Solvents which form an azeotrope with secondarily produced water and are separated into two layers upon cooling are preferred, examples of which include benzene, toluene and xylene.

The desired allyl ether compound (2) can be obtained by removing the catalyst, unreacted starting compound, etc. from the thus obtained reaction mixture solution by alkali washing, water washing, filtration, etc. and occasionally by conducting a purification through, for example, distillation in the presence of conventional polymerization inhibitor.

Further, the allyl ether compound (2) can be synthesized by subjecting to a transesterification reaction an ester (4-c) represented by the formula:

$$R^3-OCO-X-COO-R^4 \quad (4-c)$$

wherein X represents —CH=CH— or —CH$_2$—C(=CH$_2$)— and each of R$^3$ and R$^4$, as mentioned above, independently represents an alkenyl group or alkyl group having 1 to 3 carbon atoms, and the alcohol (alcohol (5)) represented by the above formula (5).

This ester (4-c) is a lower alkyl ester or lower alkenyl ester of an unsaturated dicarboxylic acid such as maleic acid, fumaric acid or itaconic acid. The ester (4-c) is, for example, one which contains an alkyl or alkenyl group having 1 to 3 carbon atoms. Specifically, for example, the ester (4-c) includes:

lower alkyl esters of maleic acid, such as dimethyl maleate, diethyl maleate, dipropyl maleate, diisopropyl maleate and diallyl maleate;

lower alkyl esters of fumaric acid, such as dimethyl fumarate, diethyl fumarate, dipropyl fumarate, diisopropyl fumarate and diallyl fumarate; and lower alkyl esters of itaconic acid, such as dimethyl itaconate, diethyl itaconate, dipropyl itaconate, diisopropyl itaconate and diallyl itaconate. With respect to the alkyl or alkenyl ester having 4 or more carbon atoms, the removal of by-products from the reaction system tends to be difficult because the boiling point of alkyl alcohol or alkenyl alcohol secondarily produced with the advance of the reaction is high.

The alcohol represented by the above formula (5), i.e., polyalkylene glycol monoallyl ether or polycycloalkylene glycol monoallyl ether having the allyl ether group is the same as described above.

The above alcohol (5) is used in an amount of 1 to 10-fold mol, preferably 1.1 to 3-fold mol, relative to the ester group equivalent of the ester (4-c), namely the ester group equivalent of the lower alkyl ester or lower alkenyl ester of unsaturated dicarboxylic acid such as maleic acid, fumaric acid or itaconic acid.

Conventional transesterification catalysts can be used in this transesterification reaction. Examples of preferably used catalysts include:

alkali metals, alkaline earth metals, oxides of these and weak acid salts thereof;

oxides, hydroxides, alcoholates, organic acid salts and acetylacetonato complexes of Mn, Zn, Zr, Cd, Ti, Pb, Co and Sn; and dibutyltin oxide and dioctyltin oxide.

These catalysts are generally used in an amount of 0.01 to 1% by weight based on the lower alkyl or alkenyl ester of maleic acid, fumaric acid or itaconic acid (total amount thereof).

The reaction can generally be performed at 80 to 200° C. under atmospheric or superatmospheric pressure. When the reaction temperature exceeds 200° C., unfavorably, polymerization is likely to occur. During the transesterification reaction, the polymerization may be prevented by the addition of a polymerization inhibitor such as a phenolic polymerization inhibitor.

The reaction is advanced by distilling secondarily produced alkyl alcohol or alkenyl alcohol off the reaction system. The reaction can be finalized by the removal of secondarily produced alkyl alcohol or alkenyl alcohol under reduced pressure.

The above allyl ether compound (2) is an intermediate (raw material) of the propenyl ether compound of the formula (1) according to the present invention, as described above. However, this allyl ether compound (2) itself can be cured in the presence of a radical polymerization initiator by heat, ultraviolet, electron beam, etc., so that it can be used as a curable resin. In the present invention, from the viewpoint of, for example, the ease of polymerization, it is preferred that the allyl ether compound (2) be isomerized for use as the propenyl ether compound of the formula (1).

Production of Propenyl Ether Compound (1) by Isomerization of Allyl Ether Compound (2)

The propenyl ether compound for use in radical polymerization (1) is obtained by the isomerization of the thus obtained allyl ether compound (2). The isomerization is generally conducted in the presence of a catalyst.

Examples of suitable isomerization catalysts include salts of the metals of Group 8 of the periodic table, complexes thereof having a ligand of, for example, phosphine, nitrile, carbonyl or alkene and catalysts comprising these metals supported on a carrier such as silica, alumina, silica-alumina, active carbon or a metal oxide. These catalysts may be employed either individually or in combination.

In particular, complexes comprising a transition metal such as ruthenium, palladium, rhodium, platinum or iridium among the metals of Group 8 of the periodic table and a ligand of, for example, phosphine, nitrile, carbonyl or alkene and catalysts comprising these metals supported on a carrier such as silica, alumina, silica-alumina, active carbon or a metal oxide are preferred in the present invention.

Specifically, the catalyst of salt of metal of Group 8 of the periodic table is, for example, ruthenium chloride or palladium chloride.

Among the catalysts of complex of metal of Group 8 of the periodic table, ruthenium complexes and palladium complexes are preferred from the viewpoint of isomerization ratio. Specifically, suitable use can be made of, for example, ruthenium complexes such as dichlorotris(triphenylphosphine)ruthenium, dichlorotetrakis(triphenylphosphine)ruthenium, dihydridotetrakis(triphenylphosphine)ruthenium, chlorohydridotris(triphenylphosphine)ruthenium, carbonylchlorohydridotris(triphenylphosphine)ruthenium and carbonyldihydridotris(triphenylphosphine)ruthenium; and palladium complexes such as dichlorobis(benzonitrile)palladium, carbonyltris(triphenylphosphine)palladium, dichlorobis(trialkylphosphine)palladium, di-$\mu$-chlorobis($\eta$-ethylene)dipalladium, di-$\mu$-dichlorobis(triphenylphosphine)dipalladium, tetrakis(triphenylphosphine)palladium, dichloro(1,5-cyclooctadiene)palladium and dichloro(1,3-norbornadiene)palladium. These catalysts can be employed either individually or in combination.

Among the catalysts comprising the above metals supported on carriers, palladium catalysts exhibit high activity. Specifically, palladium/alumina and palladium/active carbon are preferred from the viewpoint of conversion ratio.

Among the above catalysts, the metal salt catalyst and the metal complex catalyst are generally used in an amount of 0.01 to 10% by weight, preferably 0.1 to 5% by weight, based on the allyl ether compound (2). The reaction is generally performed at 30 to 250° C., preferably 100 to 200° C. When the reaction temperature is lower than 30° C., the reaction rate is too low. On the other hand, when the reaction temperature exceeds 250° C., side reactions may occur.

In the use of the catalysts comprising the above metals supported on carriers, the catalyst supporting 0.05 to 10% by weight of metal is generally used in an amount of 0.01 to 50% by weight, preferably 5 to 20% by weight, based on the allyl ether compound (2). The reaction is generally performed at 30 to 250° C., preferably 100 to 200° C. When the reaction temperature is lower than 30° C., the reaction rate is too low. On the other hand, when the reaction temperature exceeds 250° C., side reactions may occur.

The isomerization reaction can be performed in an atmosphere of inert gas such as nitrogen gas.

Further, the isomerization reaction can be performed in any of various solvents.

Examples of the solvents include:

aromatic hydrocarbons such as benzene, toluene and xylene;

ethers such as diethyl ether, dimethoxyethane, methoxyethyl ether and tetrahydrofuran;

esters such as ethyl acetate, propyl acetate and butyl acetate;

ketones such as acetone and methyl ethyl ketone; and alcohols such as methanol, ethanol, isopropyl alcohol and n-butyl alcohol.

A polymerization inhibitor can be added in order to prevent the occurrence of polymerization reaction during the isomerization reaction.

Examples of suitable polymerization inhibitors include:

quinones such as p-benzoquinone and 2,5-diphenyl-p-benzoquinone;

phenols such as hydroquinone, p-t-butylcatechol, 2,5-di-t-butylhydroquinone, mono-t-butylhydroquinone and tetrakis[methylene-3-(3,5-di-t-butyl-4-hydroxyphenyl) propionato]methane; and metal salts such as copper naphthenate and cobalt naphthenate.

During this isomerization reaction, the isomerization of a maleate to a fumarate may occur depending on the conditions such as the type and amount of catalyst and reaction temperature. In this isomerization reaction, not only a complete isomerization of the maleate to the fumarate may occur but also the isomerization to an isomer mixture consisting of the maleate and the fumarate may result. In the present invention, both of these can be used as the ether compound for use in radical polymerization (1). Further, there is no particular limitation with respect to the isomer ratio.

In the isomerization of the allyl ether compound of the formula (2), when the ratio of isomerization of allyl ether group to the corresponding propenyl ether group is less than 100%, the obtained isomer has both allyl ether group and propenyl ether group. This compound is also a useful ether compound for use in radical polymerization.

From the viewpoint of the ease of radical polymerization of the ether compound for use in radical polymerization, it is preferred that the ratio of isomerization of allyl ether of the formula (2) to propenyl ether of the formula (1) be at least 50%. This isomerization ratio can be determined by, for example, characteristic peak integral ratio of an allyl ether group vs. propenyl ether group measured by $^1$H-NMR.

Although the product obtained by the isomerization can be used as it is, occasionally it may be purified before use by, for example, distillation in the presence of a polymerization inhibitor such as a phenol or copper naphthenate.

Curing of Propenyl Ether Compound for Use in Radical Polymerization (1)

The thus obtained propenyl ether compound of the present invention can easily be cured by heating or irradiating it with ultraviolet rays or electron beams to thereby effect a radical polymerization in the presence of a radical polymerization initiator.

A wide variety of radical polymerization initiators can be used without any particular limitation as long as radicals are formed by heat, ultraviolet rays, electron beams, radiation, etc.

Examples of radical polymerization initiators which can be used in the radical polymerization by heat include:

azo compounds such as 2,2'-azobisisobutyronitrile and 2,2'-azobisisovaleronitrile;

ketone peroxides such as methyl ethyl ketone peroxide, methyl isobutyl ketone peroxide and cyclohexanone peroxide;

diacyl peroxides such as benzoyl peroxide, decanoyl peroxide and lauroyl peroxide;

dialkyl peroxides such as dicumyl peroxide, t-butyl cumyl peroxide and di-t-butyl peroxide;

peroxyketals such as 1,1-di-t-butylperoxycyclohexane and 2,2-di(t-butylperoxy)butane;

alkyl peresters such as t-butyl peroxypivalate, t-butyl peroxy-2-ethylhexanoate, t-butyl peroxyisobutyrate, di-t-butyl peroxyhexahydroterephthalate, di-t-butyl peroxyazelate, t-butyl peroxy-3,5,5-trimethylhexanoate, t-butyl peroxyacetate, t-butyl peroxybenzoate and di-t-butyl peroxytrimethyladipate; and percarbonates such as diisopropyl peroxydicarbonate, di-sec-butyl peroxydicarbonate and t-butyl peroxyisopropylcarbonate.

These radical polymerization initiators can be employed either individually or in combination.

Examples of radical polymerization initiators which can be used in the radical polymerization by irradiation with ultraviolet rays, electron beams or radiation include:

acetophenones and derivatives thereof, such as acetophenone, 2,2-dimethoxy-2-phenylacetophenone, diethoxyacetophenone, 1-hydroxycyclohexyl phenyl ketone, 2-methyl-1-[4-(methylthio)phenyl]-2-morpholinopropanone-1, 2-benzyl-2-dimethylamino-1-(4-morpholinophenyl)-butanone-1 and 2-hydroxy-2-methyl-1-phenylpropan-1-one; benzophenone and derivatives thereof, such as benzophenones, 4,4'-bis(dimethylamino)benzophenone, 4-trimethylsilylbenzophenone and 4-benzoyl-4'-methyldiphenyl sulfide;

benzoins and derivatives thereof, such as benzoin, benzoin ethyl ether, benzoin propyl ether, benzoin isobutyl ether and benzoin isopropyl ether; and methylphenyl glyoxylate, benzoin dimethylketal and 2,4,6-trimethylbenzoyldiphenylphosphine oxide. These radical polymerization initiators can be employed either individually or in combination.

These radical polymerization initiators are generally used in an amount of 0.01 to 15% by weight, preferably 0.1 to 10% by weight, based on the weight of the ether compound (1) of the present invention.

The ether compound (1) of the present invention may be blended before use with, for example, an ultraviolet absorber, an antioxidant, a colorant, a filler, a release agent, an antistatic agent and various stabilizers, depending on the object of use.

The propenyl ether compound (1) for use in radical polymerization according to the present invention can be widely utilized in the field of curable resins, for example, used in:

coating materials for wood coating, film coating, metal coating, plastic coating, inorganic coating, hard coating and optical fiber coating;

paint materials such as paints and printing inks; photoforming materials; optical materials such as optical disks, spectacle lenses and prisms; adhesives; photoresist; sealants; and molding compounds.

EFFECT OF THE INVENTION

The novel propenyl ether compound and novel allyl ether compound of the present invention are extremely useful because, as apparent from the Examples, these can be cured by the simple radical polymerization by heat or photoirradiation, and they are applicable for the above various uses such as coating materials, paint materials, optical materials and adhesives.

The present invention provides the process for efficiently and easily producing the above ether compounds.

EXAMPLE

The present invention will be further illustrated below with reference to the following Examples, which in no way limit the scope of the invention as long as the spirit of the invention is not departed from. The following measuring instruments were used.

$^1$H-NMR;

Employed model: JEOL EX-400 (400 MHz).

Each sample was dissolved in deuterated chloroform, and the chemical shift was computed with the use of tetramethylsilane as an internal reference substance.

IR;
Employed model: FT/IR-7300, manufactured by Japan Spectroscopic Co., Ltd.
UV irradiation apparatus;
Employed model: Toscure 401, manufactured by Toshiba Corporation (mercury lamp, irradiation intensity: irradiation distance 100 mm-70 mW/cm$^2$).

EXAMPLE 1

144 g (1 mol) of dimethyl fumarate, 245 g (2.4 mol) of ethylene glycol monopropenyl ether, 0.2; g of zinc acetate and 0.3 g of tetrakis[methylene-3-(3,5-di-t-butyl-4-hydroxyphenyl)propionato]methane (trade name "Irganox 1010" available from Japan Ciba-Geigy, hereinafter also referred to simply as "Irganox 1010") as a polymerization inhibitor were charged into a 1 lit. flask equipped with distillation column. The mixture was heated at 140° C. in a nitrogen atmosphere, and a reaction was effected for 8 hr. Secondarily produced methanol was distilled off. When the amount of methanol reached 70% of the theoretical amount, the pressure inside the reaction system was gradually reduced to thereby accelerate the removal of methanol by distillation. The pressure was finally reduced to about 400 Pa, thereby completely distilling off the theoretical amount of methanol and any remaining ethylene glycol monopropenyl ether. The reaction mixture was cooled to room temperature, and 283 g of product was recovered. The obtained product was analyzed by $^1$H-NMR and IR, and it was found that the product was bis[2-(1-propenyloxy)ethyl] fumarate.

$^1$H-NMR; δ(ppm) 6.91 (s, 2H, —OCOCH̲=CH̲COO—), 6.23, 5.95 (d, 2H, CH$_3$—CH=CH̲—O—), 4.83–4.78, 4.47–4.42 (m, 2H, CH$_3$—CH̲=CH—O—), 4.42–4.35 (m, 4H, —O—CH$_2$—CH̲$_2$—OCO—), 3.99–3.96, 3.90–3.87 (m, 4H, —O—CH̲$_2$—CH$_2$—OCO—), 1.57, 1.56 (d, 6H, CH̲$_3$—CH=CH—O—).

IR; ν(CO)=1725 cm$^{-1}$, ν(propenyl C=C)=1670 cm$^{-1}$, ν(fumarate C=C)=1660 cm$^{-1}$.

1-Hydroxycyclohexyl phenyl ketone (trade name "Irgacure 184" available from Japan Ciba-Geigy, hereinafter also referred to simply as "Irgacure 184") as a radical polymerization initiator was added to the obtained product in an amount of 4% by weight based on the weight of the product and mixed. The mixture was applied to a glass plate so that the coating thickness was about 15 μm. Thereafter, the coating was irradiated ith UV by means of conveyor-type UV irradiation pparatus equipped with mercury lamps to thereby effect a radical polymerization reaction, so that the coating was cured. In this curing, the coating was passed once through the apparatus at a conveyor speed of 0.5 m/min. As a result, a tack-free cured film was obtained.

EXAMPLE 2

144 g (1 mol) of dimethyl fumarate, 245 g (2.4 mol) of ethylene glycol monoallyl ether, 0.2 g of zinc acetate and 0.05 g of Irganox 1010 as a polymerization inhibitor were charged into a 1 lit. flask equipped with distillation column. The mixture was heated at 140° C. in a nitrogen atmosphere for 8 hr. Secondarily produced methanol was distilled off. When the amount of methanol reached 70% of the theoretical amount, the pressure inside the reaction system was gradually reduced to thereby accelerate the removal of methanol by distillation. The pressure was finally reduced to about 400 Pa, thereby completely distilling off the theoretical amount of methanol and any remaining ethylene glycol monoallyl ether. The reaction mixture was cooled to room temperature, and 283 g of product was recovered. The obtained product was analyzed by $^1$H-NMR and IR, and it was found that the product was bis(2-allyloxyethyl) fumarate.

$^1$H-NMR; δ(ppm) 6.90 (s, 2H, —OCOCH̲=CH̲COO—), 5.95–5.85 (m, 2H, CH$_2$=CH̲—CH$_2$—), 5.28 (dt, 2H, CH̲$_2$=CH—CH$_2$—), 5.19 (dt, 2H, CH̲$_2$=CH—CH$_2$—), 4.32 (t, 4H, —O—CH$_2$CH̲$_2$—OCO—), 4.00 (d, 4H, CH$_2$=CH-CH̲$_2$—), 3.70 (t, 4H, —O—CH̲$_2$CH$_2$—OCO—).

IR; ν(CO)=1730 cm$^{-1}$, ν(fumarate C=C)=1660 cm$^{-1}$, ν(allyl C=C)=1646 cm$^{-1}$.

28 g of the obtained bis(2-allyloxyethyl) fumarate and 0.1 g of dihydridotetrakis(triphenylphosphine)ruthenium were charged into a 50 ml flask equipped with a condenser. The inside of the reaction vessel was deaerated and purged with nitrogen. A reaction was carried out at 140 to 150° C. in a nitrogen atmosphere for 5 hr.

Thereafter, 0.03 g of the above polymerization inhibitor Irganox 1010 was added to the reaction mixture, and purification was performed by vacuum distillation. 20 g of product was obtained by distillation at 150 to 155° C./133 Pa. The obtained product was analyzed by $^1$H-NMR and IR, and it was found that the product was the same bis[2-(1-propenyloxy)ethyl] fumarate as in Example 1.

$^1$H-NMR δ(ppm) 6.91 (s, 2H, —OCOCH̲=CH̲COO—), 6.23, 5.95 (d, 2H, CH$_3$—CH=CH̲—O—), 4.83–4.78, 4.47–4.42 (m, 2H, CH$_3$—CH̲=CH—O—), 4.42–4.35 (m, 4H, —O—CH$_2$—CH̲$_2$—OCO—), 3.99–3.96, 3.90–3.87 (m, 4H, —O—CH̲$_2$CH$_2$—OCO—), 1.57, 1.56 (d, 6H, CH̲$_3$—CH=CH—O—).

IR; ν(CO)=1725 cm$^{-1}$, ν(propenyl C=C)=1670 cm$^{-1}$, ν(fumarate C=C)=1660 cm$^{-1}$.

In the same manner as in Example 1, the above radical polymerization initiator Irgacure 184 was added to the obtained product in an amount of 4% by weight based on the weight of the product and mixed. The mixture was applied to a glass plate so that the coating thickness was 15 μm. Thereafter, the coating was cured with UV by means of the above UV irradiation apparatus. In this curing, the coating was passed once through the apparatus at a conveyor speed of 0.5 m/min. As a result, a tack-free cured film was obtained.

EXAMPLE 3

98 g (1 mol) of maleic anhydride, 245 g (2.4 mol) of ethylene glycol monoallyl ether, 200 ml of benzene and 0.5 g of sulfuric acid were charged into a 1 lit. glass flask equipped with an agitator, a thermometer, a condenser and a water determining receiver. The mixture was heated on an oil bath under agitation. The reaction temperature was raised to 80° C., and the reaction was continued while distilling off water secondarily produced in accordance with the progress of the reaction. When the amount of water distilled off reached the theoretical amount, the reaction was terminated, followed by cooling. The thus obtained reaction mixture was transferred into a separatory funnel. 300 ml of benzene was added thereto, and separatory washing was conducted with the use of a 10% aqueous sodium carbonate solution and water. Thereafter, the reaction mixture was purified by vacuum distillation. 241 g of product was obtained by distillation at 150 to 155° C./133 Pa.

The obtained product was analyzed by 1H-NMR and IR, and it was found that the product was bis(2-allyloxyethyl) maleate.

¹H-NMR; δ(ppm) 6.30 (s, 2H, —OCOCH═CHCOO—), 5.95–5.85 (m, 2H, CH₂═CH—CH₂—), 5.28 (dt, 2H, CH₂═CH—CH₂—), 5.19 (dt, 2H, CH₂═CH—CH₂—), 4.34 (t, 4H, —O—CH₂CH₂—OCO—), 4.02 (d, 4H, CH₂═CH—CH₂—), 3.68 (t, 4H, —O—CH₂CH₂—OCO—).

IR; ν(CO)=1732 cm⁻¹, ν(allyl C═C, maleate C═C)= 1646 cm⁻¹.

28 g of the thus obtained bis(2-allyloxyethyl) maleate and 0.1 g of dichlorotris(triphenylphos phine)ruthenium were charged into the same reaction vessel as in Example 2, and a reaction was carried out at 150° C. in a nitrogen atmosphere for 7 hr. Thereafter, 0.03 g of the above polymerization inhibitor Irganox 1010 was added to the reaction mixture, and the reaction mixture was purified by vacuum distillation. 18 g of product was obtained by distillation at 150 to 155° C./133 Pa. The obtained product was analyzed by ¹H-NMR and IR, and it was found that the product was the same bis[2-(1-propenyloxy)ethyl] fumarate as in Example 1, which resulted from the isomerization of maleate to fumarate.

¹H-NMR; δ(ppm) 6.91 (s, 2H, —OCOCH═CHCOO—), 6.23, 5.95 (d, 2H, CH₃—CH═CH—O—), 4.83–4.78, 4.47–4.42 (m, 2H, CH₃—CH═CH—O—), 4.42–4.35 (m, 4H, —O—CH₂CH₂—OCO—), 3.99–3.96, 3.90–3.87 (m, 4H, —O—CH₂CH₂—OCO—), 1.57, 1.56 (d, 6H, CH₃—CH═CH—O—).

IR; ν(CO)=1725 cm⁻¹, ν(propenyl C═C)=1670 cm⁻¹, ν(fumarate C═C)=1660 cm⁻¹.

In the same manner as in Example 1, the above radical polymerization initiator Irgacure 184 was added to the obtained product in an amount of 4% by weight based on the weight of the product and mixed. The mixture was applied to a glass plate so that the coating thickness was 15 μm. Thereafter, the coating was cured with WV by means of the above UV irradiation apparatus. In this curing, the coating was passed once through the apparatus at a conveyor speed of 0.5 m/min. As a result, a tack-free cured film was obtained.

EXAMPLE 4

98 g (1 mol) of maleic anhydride, 256 g (2.2 mol) of propylene glycol monoallyl ether, 200 ml of benzene and 0.5 g of sulfuric acid were charged into a 1 lit. glass flask equipped with an agitator, a thermometer, a condenser and a water determining receiver. The mixture was heated on an oil bath under agitation. The reaction temperature was raised to 80° C., and the reaction was continued while distilling off water secondarily produced in accordance with the progress of the reaction. When the amount of water distilled off reached the theoretical amount, the reaction was terminated, followed by cooling. The thus obtained reaction mixture was transferred into a separatory funnel. 300 ml of benzene was added thereto, and separatory washing was conducted with the use of a 10% aqueous sodium carbonate solution and water. Thereafter, a vacuum concentration of the reaction mixture was performed, thereby obtaining 300 g of product.

The obtained product was analyzed by ¹H-NMR and IR, and it was found that the product was bis(3-allyloxypropyl) maleate.

¹H-NMR; δ(ppm) 6.30 (s, 2H, —OCOCH═CHCOO—), 5.96–5.85 (m, 2H, CH₂═CH—CH₂—), 5.26 (dt, 2H, CH₂═CH—CH₂—), 5.21 (dt, 2H, CH₂═CH—CH₂—), 4.82 (t, 2H, —O—CH₂—CH₂—CH₂—OCO—), 4.30 (d, 4H, CH₂═CH—CH₂—), 4.10–4.00 (m, 4H, —O—CH₂—CH₂—CH₂—OCO—), 3.68 (t, 4H, —O—CH₂—CH₂—CH₂—OCO—).

IR; ν(CO)=1732 cm⁻¹, ν(allyl C═C, maleate C═C)= 1645 cm⁻¹. Dicumyl peroxide as a radical polymerization initiator was mixed into the obtained product in an amount of 2% by weight based on the weight of the product and dissolved. The mixture was cast into the interstice of two cellophane laminated glass plates having a silicon-made spacer interposed therebetween, placed in an oven and heated at 110° C. for 30 min, at 130° C. for 1 hr and at 160° C. for 1 hr. A cured product having a Barcol hardness of 30 was obtained by this casting and curing.

EXAMPLE 5

144 g (1 mol) of dimethyl fumarate, 279 g (2.4 mol) of propylene glycol monoallyl ether, 0.3 g of dibutyltin oxide and 0.05 g of polymerization inhibitor Irganox 1010 were charged into a 1 lit. internal volume flask equipped with distillation column. The mixture was heated at 150° C. in a nitrogen atmosphere. Secondarily produced methanol was distilled off. When the amount of methanol reached 70% of the theoretical amount, the pressure inside the reaction system was gradually reduced to thereby accelerate the removal of methanol by distillation. The pressure was finally reduced to about 400 Pa, thereby completely distilling off the theoretical amount of methanol and any remaining propylene glycol monoallyl ether.

The reaction mixture was cooled to room temperature, and 315 g of product was recovered. The obtained product was analyzed by ¹H-NMR and IR, and it was found that the product was bis(3-allyloxypropyl) fumarate.

¹H-NMR; δ(ppm) 6.90 (s, 2H, —OCOCH═CHCOO—), 5.96–5.84 (m, 2H, CH₂═CH—CH₂—), 5.26 (dt, 2H, CH₂═CH—CH₂—), 5.22 (dt, 2H, CH₂═CH—CH₂—), 4.82 (t, 2H, —O—CH₂—CH₂—CH₂—OCO—), 4.30 (d, 4H, CH₂═CH—CH₂—), 4.10–4.00 (m, 4H, —O—CH₂—CH₂—CH₂—OCO—), 3.68 (t, 4H, —O—CH₂—CH₂—CH₂—OCO—).

IR; ν(CO)=1732 cm⁻¹, ν(fumarate C═C)=1660 cm⁻¹, ν(allyl C═C)=1645 cm⁻¹.

In the same manner as in Example 4, dicumyl peroxide as a radical polymerization initiator was mixed into the obtained product in an amount of 2% by weight based on the weight of the product and dissolved. The mixture was cast and heated at 110° C. for 30 min, at 130° C. for 1 hr and at 160° C. for 1 hr. A cured product having a Barcol hardness of 35 was obtained by this casting and curing.

EXAMPLE 6

172 g (1 mol) of dimethyl fumarate, 306 g (3 mol) of ethylene glycol monopropenyl ether, 0.2 g of dibutyltin oxide and 0.05 g of polymerization inhibitor Irganox 1010 were charged into a 1 lit. flask equipped with distillation column. The mixture was heated at 150° C. in a nitrogen atmosphere to thereby react it. Secondarily produced ethanol was distilled off. When the amount of ethanol reached 70% of the theoretical amount, the pressure inside the reaction system was gradually reduced to thereby accelerate the removal of ethanol by distillation. The pressure was finally reduced to about 400 Pa, thereby completely distilling off the theoretical amount of ethanol and any remaining ethylene glycol monopropenyl ether. The reaction mixture was cooled to room temperature, and 283 g of product was recovered. The obtained product was analyzed by ¹H-NMR and IR, and it was found that the product was bis[2-(1-propenyloxy)ethyl] fumarate.

¹H-NMR; δ(ppm) 6.91 (s, 2H, —OCOCH═CHCOO—), 6.23, 5.95 (d, 2H, CH₃—CH═CH—O—), 4.83–4.78, 4.47–4.42 (m, 2H, CH$_3$—CH=C$\underline{H}$—O—), 4.42–4.35 (m, 4H, —O—CH$_2$—C$\underline{H}_2$—OCO—), 3.99–3.96, 3.90–3.87 (m, 4H, —O—C$\underline{H}_2$—CH$_2$—OCO—), 1.57, 1.56 (d, 6H, C$\underline{H}_3$—CH=CH—O—).

IR; ν(CO)=1725 cm$^{-1}$, ν(propenyl C=C)=1670 cm$^{-1}$, ν(fumarate C=C)=1660 cm$^{-1}$.

In the same manner as in Example 4, dicumyl peroxide as a radical polymerization initiator was mixed into the obtained product in an amount of 2% by weight based on the weight of the product and dissolved. The mixture was cast and heated at 110° C. for 30 min, at 130° C. for 1 hr and at 160° C. for 1 hr. A cured product having a Barcol hardness of 39 was obtained by this casting and curing.

EXAMPLE 7

449 g (2.8 mol) of dimethyl itaconate, 870 g (5.7 mol) of ethylene glycol monopropenyl ether and 1.32 g of dibutyltin oxide were charged into a 1 lit. flask equipped with distillation column. The mixture was heated at 150° C. in a nitrogen atmosphere to thereby react it. Secondarily produced methanol was distilled off. When the amount of methanol reached 70% of the theoretical amount, the pressure inside the reaction system was gradually reduced to thereby accelerate the removal of methanol by distillation. The pressure was finally reduced to about 400 Pa, thereby completely distilling off the theoretical amount of methanol and any remaining ethylene glycol monopropenyl ether. The reaction mixture was cooled to room temperature, and 830 g of product was recovered. The obtained product was analyzed by $^1$H-NMR and IR, and it was found that the product was bis[2-(1-propenyloxy)ethyl] itaconate.

$^1$H-NMR; δ(ppm) 6.37 (s, 1H, =C=C$\underline{H}_2$), {6.22 (d, CH$_3$—CH=C$\underline{H}$—O—), 5.98–5.91 (m, CH$_3$—C=C$\underline{H}$—O—), total 2H}, {4.82 4.65 (m, CH$_3$—C$\underline{H}$=CH—O—), 4.48–4.37 (m, CH$_3$—CH=C$\underline{H}$—O—), total 2H}, 4.37–4.23 (m, 4H, —O—CH$_2$C$\underline{H}_2$—OCO—), 3.97–3.80 (m, 4H, —O—C$\underline{H}_2$CH$_2$—OCO—), 3.38 (s, 2H, —OCO—C$\underline{H}_2$—C=CH$_2$), 1.58–1.51 (m, 6H, C$\underline{H}_3$—CH=CH—O—).

IR; ν(CO)=1740 cm$^{-1}$, ν(propenyl C=C)=1670 cm$^{-1}$, ν(itaconate C=C)=1643 cm$^{-1}$.

In the same manner as in Example 1, the above radical polymerization initiator Irgacure 184 was added to the obtained product in an amount of 5% by weight based on the weight of the product and mixed. The mixture was applied to a glass plate so that the coating thickness was 15 μm. Thereafter, the coating was cured with UV by means of the above UV irradiation apparatus. In this curing, the coating was passed four times through the apparatus at a conveyor speed of 0.5 m/min. As a result, a tack-free cured film was obtained.

EXAMPLE 8

250 g (0.88 mol) of bis(2-allyloxyethyl) maleate obtained by the process described in Example 3, 28 g of 5% Pd-Al$_2$O$_3$ and 153 g of toluene were charged into a 500 ml flask equipped with reflux device and refluxed in a nitrogen atmosphere for 5 hr. The reaction mixture was cooled to room temperature, and 5% Pd-Al$_2$O$_3$ was filtered off. The obtained filtrate was concentrated in vacuum, and 250 g of product was recovered. The obtained product was analyzed by $^1$H-NMR and IR, and it was found that the product was bis[2-(1-propenyloxy)ethyl] maleate.

$^1$H-NMR; δ(ppm) 6.30 (s, 2H, —OCOC$\underline{H}$=C$\underline{H}$COO—), 6.23, 5.95 (d, 2H, CH$_3$—CH=C$\underline{H}$—O—), 4.83–4.75, 4.51–4.40 (m, 2H, CH$_3$—C$\underline{H}$=CH—O—), 4.40–4.34 (m, 4H, —O—CH$_2$C$\underline{H}_2$—OCO—), 3.96, 3.87 (t, 4H, —O—C$\underline{H}_2$CH$_2$—OCO—), 1.59–1.54 (m, 6H, C$\underline{H}_3$—CH=CH—O—).

IR; ν(CO)=1732 cm$^{-1}$, ν(propenyl C=C)=1670 cm$^{-1}$, ν(maleate C=C)=1645 cm$^{-1}$.

In the same manner as in Example 1, the above radical polymerization initiator Irgacure 184 was added to the obtained product in an amount of 4% by weight based on the weight of the product and mixed. The mixture was applied to a glass plate so that the coating thickness was 15 μm. Thereafter, the coating was cured with UV by means of the above UV irradiation apparatus. In this curing, the coating was passed thrice through the apparatus at a conveyor speed of 0.5 m/min. As a result, a tack-free cured film was obtained.

EXAMPLE 9

400 g (2.8 mol) of dimethyl maleate, 850 g (8.3 mol) of ethylene glycol monopropenyl ether, 1.3 g of dibutyltin oxide and 0.25 g of polymerization inhibitor Irganox 1010 were charged into a 2 lit. flask equipped with distillation column. The mixture was heated at 150° C. in a nitrogen atmosphere to thereby react it. Secondarily produced methanol was distilled off. When the amount of methanol reached 70% of the theoretical amount, the pressure inside the reaction system was gradually reduced to thereby accelerate the removal of methanol by distillation. The pressure was finally reduced to about 400 Pa, thereby completely distilling off the theoretical amount of methanol and any remaining ethylene glycol monopropenyl ether. The reaction mixture was cooled to room temperature, and 790 g of product was recovered. The obtained product was analyzed by $^1$H-NMR and IR, and it was found that the product was the same bis[2-(1-propenyloxy)ethyl] maleate as in Example 8.

$^1$H-NMR; δ(ppm) 6.30 (s, 2H, —OCOC$\underline{H}$=C$\underline{H}$COO—), 6.23, 5.95 (d, 2H, CH$_3$—CH=C$\underline{H}$—O—), 4.83–4.75, 4.51–4.40 (m, 2H, CH$_3$—C$\underline{H}$=CH—O—), 4.40–4.34 (m, 4H, —O—CH$_2$C$\underline{H}_2$—OCO—), 3.96, 3.87 (t, 4H, —O—C$\underline{H}_2$CH$_2$—OCO—), 1.59–1.54 (m, 6H, C$\underline{H}_3$—CH=CH—O—).

IR; ν(CO)=1732 cm$^{-1}$, ν(propenyl C=C)=1670 cm$^{-1}$, ν(maleate C=C)=1645 cm$^{-1}$.

In the same manner as in Example 4, dicumyl peroxide was mixed into the obtained product in an amount of 2% by weight based on the weight of the product. The mixture was cast and cured at 110° C. for 30 min, at 130° C. for 1 hr and at 160° C. for 1 hr. Thus, a cured product having a Barcol hardness of 40 was obtained.

EXAMPLE 10

208.6 g (0.73 mol) of bis(2-allyloxyethyl) maleate obtained by the process described in Example 3 and 22.3 g of 5% Pd-Al$_2$O$_3$ were charged into a 300 ml flask and heated at 150° C. in a nitrogen atmosphere for 10 hr to thereby effect a reaction. The reaction mixture was cooled to room temperature, and 5% Pd-Al$_2$O$_3$ was filtered off. Thus, 200 g of product was recovered. The obtained product was analyzed by $^1$H-NMR and IR, and it was found that the product was the same bis[2-(1-propenyloxy)ethyl] maleate as in Example 8.

$^1$H-NMR; δ(ppm) 6.30 (s, 2H, —OCOC$\underline{H}$=C$\underline{H}$COO—), 6.23, 5.95 (d, 2H, CH$_3$—CH=C$\underline{H}$—O—), 4.83–4.75, 4.51–4.40 (m, 2H, CH$_3$—C$\underline{H}$=CH—O—), 4.40–4.34 (m, 4H, —O—CH$_2$C$\underline{H}_2$—OCO—), 3.96, 3.87 (t, 4H, —O—C$\underline{H}_2$CH$_2$ OCO—), 1.59–1.54 (m, 6H, C$\underline{H}_3$—CH=CH—O—).

IR; ν(CO)=1732 cm$^{-1}$, ν(propenyl C=C)=1670 cm$^{-1}$, ν(maleate C=C)=1645 cm$^{-1}$.

In the same manner as in Example 1, the above radical polymerization initiator Irgacure 184 was added to the obtained product in an amount of 4% by weight based on the weight of the product and mixed. The mixture was applied to a glass plate so that the coating thickness was 15 μm. Thereafter, the coating was cured with UV by means of the above UV irradiation apparatus. In this curing, the coating was passed thrice through the apparatus at a conveyor speed of 0.5 m/min. As a result, a tack-free cured film was obtained.

EXAMPLE 11

102 g (0.36 mol) of bis(2-allyloxyethyl) maleate obtained by the process described in Example 3 and 11.4 g of 5% Pd-$Al_2O_3$ were charged into a 300 ml flask and heated at 150° C. in a nitrogen atmosphere for 3 hr to thereby effect a reaction. The reaction mixture was cooled to room temperature, and 5% Pd-$Al_2O_3$ was filtered off. Thus, 100 g of product was recovered. The obtained product was analyzed by $^1$H-NMR, and it was found from characteristic peak integral ratio of an allyl ether group ($CH_2$=CH—$CH_2O$—) vs. propenyl ether group ($CH_3CH$=CH—O—) that the product was an isomer mixture in which a compound having an allyl ether group was contained in an amount of 48%.

In the same manner as in Example 1, the above radical polymerization initiator Irgacure 184 was added to the obtained product in an amount of 4% by weight based on the weight of the product and mixed. The mixture was applied to a glass plate so that the coating thickness was 15 μm. Thereafter, the coating was cured by means of the above UV irradiation apparatus. In this curing, the coating was passed thrice through the apparatus at a conveyor speed of 0.5 m/min. As a result, a tack-free cured film was obtained.

What is claimed is:

1. A propenyl ether compound for use in radical polymerization, represented by the formula:

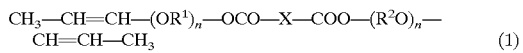
(1)

wherein X represents —CH=CH— or —$CH_2$—C(=$CH_2$)—, each of $R^1$ and $R^2$ represents an alkylene group having 2 to 4 carbon atoms or a cycloalkylene group having 5 to 12 carbon atoms, and n is an integer of 1 to 5.

2. The propenyl ether compound for use in radical polymerization as claimed in claim 1, wherein, in the formula (1), n=1 and each of $R^1$ and $R^2$ represents —$CH_2$—$CH_2$— or —$CH_2$—$CH(CH_3)$—.

3. The propenyl ether compound for use in radical polymerization as claimed in claim 1, wherein, in the formula (1), n=1, each of $R^1$ and $R^2$ represents —$CH_2$—$CH_2$— or —$CH_2$—$CH(CH_3)$—, and X represents —CH=CH— (trans).

4. A process for producing the propenyl ether compound for use in radical polymerization according to claim 1, which comprises subjecting:

an ester represented by the formula $R^3$—OCO—X—COO—$R^4$ (wherein X represents —CH=CH— or —$CH_2$—C(=$CH_2$)— and each of $R^3$ and $R^4$ independently represents an alkenyl group or alkyl group having 1 to 3 carbon atoms) and an alcohol represented by the formula $CH_3$—CH=CH—$(OR^5)_n$—OH (wherein $R^5$ represents an alkylene group having 2 to 4 carbon atoms or a cycloalkylene group having 5 to 12 carbon atoms, and n is an integer of 1 to 5)

to a transesterification reaction conducted in the presence of a transesterification catalyst.

5. A process for producing the propenyl ether compound for use in radical polymerization according to claim 1, which comprises isomerizing an allyl ether compound represented by the formula:

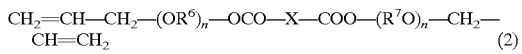
(2)

wherein X represents —CH=CH— or —$CH_2$—C(=$CH_2$)—, each of $R^6$ and $R^7$ independently represents an alkylene group having 2 to 4 carbon atoms or a cycloalkylene group having 5 to 12 carbon atoms, and n is an integer of 1 to 5.

6. A process for producing the propenyl ether compound for use in radical polymerization according to claim 1, which comprises subjecting:

(i) at least one carboxylic acid or anhydride thereof selected from the group consisting of maleic anhydride, maleic acid, fumaric acid, itaconic acid and itaconic anhydride, and (ii) an alcohol represented by the formula $CH_2$=CH—$CH_2$—$(OR^8)_n$—OH (wherein $R^8$ represents an alkylene group having 2 to 4 carbon atoms or a cycloalkylene group having 5 to 12 carbon atoms, and n is an integer of 1 to 5)

to an esterification reaction conducted in the presence of an esterification catalyst to thereby obtain the allyl ether compound of the above formula (2), and isomerizing the allyl ether compound.

7. A process for producing the propenyl ether compound for use in radical polymerization according to claim 1, which comprises subjecting:

an ester represented by the formula $R^3$—OCO—X—COO—$R^4$ (wherein X represents —CH=CH— or —$CH_2$—C(=$CH_2$)— and each of $R^3$ and $R^4$ independently represents an alkenyl group or alkyl group having 1 to 3 carbon atoms) and an alcohol represented by the formula $CH_2$=CH—$CH_2$—$(OR^8)_n$—OH (wherein $R^8$ represents an alkylene group having 2 to 4 carbon atoms or a cycloalkylene group having 5 to 12 carbon atoms, and n is an integer of 1 to 5)

to a transesterification reaction conducted in the presence of a transesterification catalyst to thereby obtain the allyl ether compound of the above formula (2), and isomerizing the allyl ether compound.

8. The process as claimed in any of claims 5 to 7, wherein the isomerization is performed in the presence of an isomerization catalyst comprising a metal salt, a metal complex, or a catalyst supporting a metal, which metal is at least one metal selected from among the metals of Group 8 of the periodic table.

9. The process as claimed in claim 8, wherein the catalyst used as the isomerization catalyst comprises a metal salt, a metal complex, or a catalyst supporting a metal, which metal is at least one metal selected from among ruthenium, palladium, rhodium, platinum and iridium.

10. The process as claimed in claim 5, wherein, in the isomerization of the allyl ether compound of the formula (2), an allyl ether group is isomerized into a propenyl ether group corresponding thereto at a conversion of at least 50%.

* * * * *